United States Patent [19]

Schumacher et al.

[11] 4,347,389

[45] Aug. 31, 1982

[54] VAPOR PHASE NITRATION OF AROMATIC COMPOUNDS

[75] Inventors: Ignatius Schumacher, Ballwin; Kang-bo Wang, Creve Coeur, both of Mo.

[73] Assignee: Monsanto Company, St. Louis, Mo.

[21] Appl. No.: 221,658

[22] Filed: Dec. 31, 1980

[51] Int. Cl.³ .................. C07C 76/02; C07C 79/10; C07C 79/12

[52] U.S. Cl. .................. 568/937; 568/938; 568/939; 568/940; 260/688

[58] Field of Search .............. 568/937, 938, 939, 940, 568/947, 948; 260/688

[56] References Cited

U.S. PATENT DOCUMENTS

| | | | |
|---|---|---|---|
| 2,109,873 | 3/1938 | Wilhelm | 568/939 |
| 2,431,585 | 11/1947 | Rout | 568/939 |
| 3,077,502 | 2/1963 | Leib | 260/646 |
| 3,180,900 | 4/1965 | Sparks | 260/646 |
| 3,922,315 | 11/1975 | Mitchell, Jr. et al. | 568/940 |
| 3,928,476 | 12/1975 | Shimada et al. | 568/937 |
| 3,957,890 | 5/1976 | Schumacher | 568/937 |
| 3,966,830 | 6/1976 | Shimada et al. | 568/937 |
| 3,979,467 | 9/1976 | Schumacher | 568/937 |
| 4,107,220 | 8/1978 | Owsley et al. | 568/937 |
| 4,112,006 | 9/1978 | Schubert et al. | 568/940 |
| 4,234,470 | 11/1980 | Lawrence | 568/937 |

FOREIGN PATENT DOCUMENTS

| | | | |
|---|---|---|---|
| 2713262 | 9/1977 | Fed. Rep. of Germany | 568/939 |
| 380639 | 8/1973 | U.S.S.R. | 568/939 |

OTHER PUBLICATIONS

McKee, R. H., et al., Ind. Eng. Chem., vol. 28, pp. 662–667 (Jun. 1936).

*Primary Examiner*—Teddy S. Gron
*Attorney, Agent, or Firm*—Wendell W. Brooks; James C. Logomasini; Stanley L. Tarter

[57] ABSTRACT

Aromatic compounds are nitrated in the vapor phase via a process comprising contacting the aromatic compound with a nitrating agent in the presence of a nitration promoting catalyst comprising a phosphorus-vanadium-oxygen complex.

21 Claims, No Drawings

VAPOR PHASE NITRATION OF AROMATIC COMPOUNDS

BACKGROUND OF THE INVENTION

1. Field of the Invention

This invention relates to a process for the vapor phase nitration of aromatic compounds. More particularly, this invention relates to a process of a vapor phase nitration of aromatic compounds in the presence of a nitration promoting catalyst comprising a phosphorous-vanadium-oxygen complex.

Nitroaromatic compounds find use as solvents, explosives, dyes, perfumes, and analytical reagents, and are important as intermediates in organic synthesis. As an example, nitroaromatic compounds are convertible by reduction into primary amines, which, in turn, are valuable intermediates in the synthesis of dyes, pharmaceuticals, photographic developers, antioxidants, and gum inhibitors.

2. Description of the Prior Art

Nitroaromatic compounds are currently produced primarily via liquid phase reactions employing mixed acids. A sulfuric acid/nitric acid mixture is the most commonly employed industrial nitrating agent. Other mixed acids for nitration of aromatic compounds are acetic acid/nitric acid mixtures as described, for example, in U.S. Pat. No. 3,180,900. In U.S. Pat. No. 3,928,476, the latter type nitration is conducted over silica-alumina or alumina supports.

Vapor phase nitration of aromatic compounds is also known in the art. The vapor phase nitration of benzene and toluene at temperatures ranging from about 275° C. to about 310° C. is described in McKee and Wilhelm, *Industrial and Engineering Chemistry*, 28(6), 662-667 (1936) and U.S. Pat. No. 2,109,873. McKee and Wilhelm catalyzed their reaction with silica gel, with best results being reported by the use of 14 mesh material. Bauxite and alumina were reported to be ineffective as catalysts in the vapor phase nitration of benzene. More recently, U.S. Pat. No. 4,107,220 described the vapor phase nitration of chlorobenzene in the presence of molecular sieve catalysts having a pore size varying from about 5 Å to about 10 Å as a means for controlling the para-to-ortho isomer distribution of nitrochlorobenzene. A suitable temperature range was reported to be from about 190° C. to about 290° C.

Although these prior art processes generally provide the desired product, the choice of available catalysts is severely limited in that each of the prior art processes uses aluminosilicates (or silica gel) as catalysts. Thus, the discovery of an alternate catalyst composition suitable for use in the vapor phase nitration of this invention would be a decided advance in the art.

SUMMARY OF THE INVENTION

This invention is directed to a process for the vapor phase nitration of aromatic compounds in the presence of a nitration promoting catalyst comprising a phosphorus-vanadium-oxygen complex. Accordingly, the primary object of this invention is to provide a vapor phase nitration process for converting aromatic compounds to the corresponding nitroaromatic compounds characterized by high aromatic compound conversion and high nitroaromatic compound selectivity.

This and other objects, aspects, and advantages of the invention will become apparent to those skilled in the art from the accompanying description and claims.

The above objects are achieved by the improved process disclosed herein for the vapor phase nitration of aromatic compounds where the aromatic compound is contacted with a nitrating agent in the vapor phase to yield the corresponding nitroaromatic compound, the improvement comprising conducting the nitration in the presence of a nitration promoting catalyst comprising a phosphorus-vanadium-oxygen complex.

DESCRIPTION OF THE PREFERRED EMBODIMENTS

In accordance with this invention, aromatic compounds are nitrated in the vapor phase via an improved process where the aromatic compound is contacted with a nitrating agent in the vapor phase to yield the corresponding nitroaromatic compound, the improvement comprising conducting the nitration in the presence of a nitration promoting catalyst comprising a phosphorus-vanadium-oxygen complex. The process is characterized by high aromatic compound conversion and high nitroaromatic compound selectivity. And, in addition, when the aromatic compounds starting material is a monosubstituted aromatic compound having an ortho-para orientation substituent, especially chlorobenzene, the observed para-to-ortho isomer distribution is a constant 2-3/1.

Aromatic compounds suitable for use in the present process are those which undergo nitration under operating conditions to yield the desired nitroaromatic compounds. Moreover, in those instances where ortho and-/or para isomers of the nitroaromatic compound are desired, the aromatic compound starting material must have an ortho-para orientation substituent such as halogen, lower alkyl, lower hydroxyalkyl, lower acetoxyalkyl, lower alkoxy, phenyl, and the like, where the term "lower alkyl" and related terms refer to substituents containing alkyl groups of 1 to 6 carbon atoms. Nonlimiting representatives of suitable aromatic compounds include aromatic hydrocarbons, such as benzene, toluene, xylenes, ethylbenzene, cumene, and the like; aromatic ethers such as anisole, phenetole, and the like; and haloraromatic compounds such as chlorobenzene, bromobenzene, iodobenzene, and the like. It has been found, however, that the process of this invention is particularly efficacious with chlorobenzene (also known as monochlorobenzene or simply MCB).

It will be apparent, of course, that monosubstituted aromatic compounds having an ortho-para orientation substitutent—toluene and chlorobenzene, for example—upon being nitrated yield a nitroaromatic compound product containing ortho, meta, and para isomers. In such instances, the ortho and para isomers generally constitute the major portion of the product, with the metal isomer being present in only trace amounts.

The nitrating agents which are employed in the process of this invention are the gaseous oxides of nitrogen higher than nitric oxide (NO) such as nitrogen dioxide ($NO_2$), dinitrogen trioxide ($N_2O_3$), and dinitrogen tetroxide ($N_2O_4$). Of these nitrating agents, nitrogen dioxide is preferred. Thus, for convenience and clarity, the process will be described with reference to the preferred nitrogen dioxide as the nitrating agent.

The nitration promoting catalyst employed in accordance with this invention is a phosphorus-vanadium-oxygen complex.

Broadly described, such complex compositions are prepared by contacting a phosphorus compound and a vanadium compound under conditions which will provide a catalyst precursor having a phosphorus to vanadium atom ratio from about 1:2 to about 2:1, and having greater than 50 atom percent of the vanadium in the tetravalent state. The catalyst precursor is recovered and formed into any of a number of suitable structures—tablets, pills, pellets, extrusions, for example—for use in a vapor phase nitration reactor. The structured catalyst precursor is thereafter calcined at calcination conditions to form the nitration promotion catalyst in accordance with this invention.

The vanadium compounds useful as a source of vanadium in the catalyst precursors are those known in the art. Suitable, but nonlimiting, vanadium compounds include: vanadium oxides, such as vanadium pentoxide, vanadium tetroxide, vanadium trioxide, and the like; vanadium oxyhalides such as vanadyl chloride, vanadyl dichloride, vanadyl trichloride, vanadyl bromide, vanadyl dibromide, vanadyl tribromide, and the like; vanadium-containing acids such as metavanadic acid, pyrovanadic acid, and the like; vanadium salts, such as ammonium metavanadate, vanadium sulfate, vanadium phosphate, vanadyl formate, vanadyl oxylate, and the like. Of these, however, vanadium pentoxide is preferred.

The phosphorus compounds useful as a source of phosphorus in the catalyst precursors also are those known to the art. Suitable phosphorus compounds include: phosphoric acids, such as orthophosphoric acid, metaphosphoric acid, and the like; phosphorus oxides, such as phosphorus pentoxide, and the like; phosphorus halides, such as phosphorus pentachloride, phosphorus oxybromide, phosphorus oxychloride, and the like; trivalent phosphorus compounds, such as phosphorous acid, phosphorus trihalides (for example, phosphorus trichloride), organic phosphites (for example, trimethyl phosphite), sometimes known as phosphonates, and the like. Of these, orthophosphoric acid and phosphorus pentoxide are preferred, with a mixture of orthophosphoric acid and phosphorous acid being most preferred.

To prepare the precursors of the catalysts used in the present invention, a suitable vanadium compound is contacted with a suitable phosphorus compound in an acid medium and the mixture is heated to dissolve the starting materials. A reducing agent is used to reduce pentavalent vanadium to tetravalent vanadium and to maintain the vanadium in the tetravalent state. As is well known to those skilled in the art, hydrohalic acid or oxalic acid solutions, which are mild reducing agents, can serve not only as the acid medium, but also as the reducing agent for the pentavalent vanadium. A trivalent phosphorus compound can also be used as a reducing agent for the pentavalent vanadium, as well as serve as a source of phosphorus to provide the catalyst precursors. Phosphorous acid is the trivalent phosphorus compound of choice for use in the preparation of the catalyst precursors in that, as noted hereinabove, it is a preferred compound, and, in addition, can serve as an acid medium for carrying out the desired reduction of the pentavalent vanadium to the tetravalent vanadium. If desired, although not actually required, a surfactant may be added to the mixture to control particle size and prevent agglomeration of the catalyst precursors during the preparation thereof. Surfactants suitable for use in the present invention are described in Mount et al, U.S. Pat. No. 4,149,992, the disclosure of which is herein incorporated by reference.

The amount of surfactant, when employed, suitable for use in the preparation of the catalyst can vary within wide limits. It has been found that the amount of surfactant should be at least about 0.05% by weight, based on the weight of the dry catalyst precursor, since at lower concentrations the effect of the surfactant is diminished considerably. On the other hand, there is no upper limit as to the amount of surfactant that can be used, although there does not seem to be any advantage in using more than about 1.0% by weight, and it is generally preferred to use between about 0.1% and about 0.5% by weight, based on the dry weight of the catalyst precursor.

The acid solution containing the phosphorus compound and the vanadium compound is heated until a blue solution is obtained, indicating that at least 50 atom percent of the vanadium is in the tetravalent state. The amount of time required to dissolve the phosphorus compound and the vanadium compound and to provide a substantial amount of vanadium in the tetravalent state and to provide the catalyst precursors varies from batch to batch, depending upon the compounds used as starting materials and the temperature at which the compounds are heated. In general, however, heating the solution to at least 100° C. for about 4 hours is sufficient. It will be apparent, however, to those skilled in the art that an aliquot of the solution can be analyzed to ensure that at least 50 atom percent of the vanadium is in the tetravalent state.

The atom ratio of phosphorus to vanadium in the starting material is important since it controls the phosphorus to vanadium atom ratio in the final catalyst. As previously indicated, the phosphorus-vanadium-oxygen catalyst precursors should contain a phosphorus to vanadium atom ratio of from about 1:2 to about 2:1. It is preferred, however, that the phosphorus-vanadium-oxygen catalyst precursors hve a phosphorus to vanadium atom ratio between about 1:1 and about 1.5:1.

After the vanadium and phosphorus compounds are contacted and a substantial amount of the vanadium is in the tetravalent state, it is necessary to recover the phosphorus-vanadium-oxygen catalyst precursors. Techniques for recovering the catalyst precursors are well known to those skilled in the art. For example, the catalyst precursors can be deposited from aqueous solution on a carrier, such as alumina or titania, or alternatively, catalyst precursors can be recovered by gentle heating to dryness to provide solid phosphorus-vanadium-oxygen catalyst precursors. This latter technique is preferred.

After the phosphorus-vanadium-oxygen catalyst precursors are recovered, they are formed into structures suitable for use in a vapor phase nitration reactor. Techniques for forming appropriate structures from precursors for use in a fluidized bed reactor or in a fixed-tube, heat-exchanger type reactor are well known to those skilled in the art. For example, the catalyst precursors can be structured for use in a fluidized bed reactor by depositing the phosphorus-vanadium-oxygen catalyst precursor on a carrier. Alternatively, dried catalyst precursors can be comminuted for use in the fluidized bed reactor. On the other hand, catalyst precursors can be structured for use in a fixed-tube, heat-exchanger type reactor by extruding a paste of the precursors through an orifice, or by prilling, by tableting, and the like the precursors.

After the phosphorus-vanadium-oxygen catalyst precursors are formed into structures which will be used in the vapor phase nitration reactor, the precursors are calcined at temperatures between about 300° C. and about 600° C. for a suitable period of time, usually at least 2 hours, in either an inert atmosphere such as nitrogen or a noble gas, or oxygen or an oxygen-containing gas such as air to convert the catalyst precursors to the catalysts of the present invention. When the calcination is carried out in an inert atmosphere, the catalyst precursor-to-catalyst conversion occurs without excessive oxidation of the tetravalent vanadium to pentavalent vanadium.

When a free-oxygen or oxygen-containing atmosphere is employed, it is preferred to calcine the catalyst precursors until about 20 atom percent to about 90 atom percent of the vanadium has been converted to pentavalent vanadium.

It will be recognized, of course, that the exact calcination conditions will depend on the method of preparing the catalyst precursors, the equipment configuration, additives to the catalyst precursors, and the like; however, it has been found that calcination at temperatures between about 400° C. and about 500° C. for about 4 hours is generally sufficient.

Further information on the preparation of phosphorus-vanadium-oxygen complex compositions suitable for use as the nitration promoting catalyst of this invention can be had by reference to the maleic anhydride-from-n-butane art—U.S. Pat. Nos. 4,111,963; 3,907,707; 3,293,268, for example—which utilizes phosphorus-vanadium-oxygen complex compositions as catalysts. This referenced art is herein incorporated by reference.

In a preferred embodiment, the nitration promoting catalyst is conditioned by pretreatment with nitrogen dioxide at operating conditions (discussed hereinbelow) to the saturation point (in the absence of aromatic compounds). Pretreatment times in general range from about 5 minutes to about 1 hour or more. The actual pretreatment time, however, will depend upon the amount or quantity and pore structure of the nitration promoting catalyst, the flow rate of the nitrogen dioxide, the operating conditions, and the like. Usually, pretreatment for about 10 minutes to about 30 minutes is sufficient. The conditioning pretreatment while not absolutely necessary, is preferred because it permits almost immediate production of the nitroaromatic compound upon introduction of the aromatic compound to the reactor. In the absence of the pretreatment, measurable nitroaromatic compound production is delayed until the nitration promoting catalyst becomes saturated with nitrogen dioxide.

The vapor phase nitration process of this invention is not limited to a specific reaction temperature since the process can be conducted at temperatures ranging from about 80° C. to about 300° C. Preferred temperatures, however, range from about 150° C. to about 225° C. with 175° C. to about 200° C. being particularly preferred. At such preferred temperatures the rate of reaction is reasonably rapid and little, if any, by-product formation occurs. It will be appreciated, however, that the particular temperature employed for a given aromatic compound will depend to some extent upon the boiling point or vaporization temperature of the particular aromatic compound. For example, when chlorobenzene, which has a boiling point of 132° C., is the aromatic compound of choice, the vapor phase nitration is conveniently carried out within the aforesaid preferred and most preferred temperature ranges. When benzene (b.p., 80° C.) is the aromatic compound of choice, the vapor phase nitration may be conducted at temperatures which encompass the entire operative temperature range, that is, from about 80° C. to about 300° C. Again, however, temperatures between about 150° C. and about 225° C. are preferred.

As previously indicated, the vapor phase nitration of this invention can be conducted at temperatures ranging from about 80° C. to about 300° C. with temperatures between about 150° C. and about 225° C. being preferred. Some advantages accruing from conducting the vapor phase nitration of this invention at the preferred temperatures include:

(a) greater selectivity to the desired nitroaromatic compound;
(b) little, if any, by-product formation (to contaminate the desired product);
(c) high material balance between reactants and products; and
(d) minimal thermal decomposition of the nitrogen dioxide.

The latter advantage [(d)] is particularly significant in that it, to a large extent, influences the remaining advantages. It, of course, is well-known in the art that at elevated temperatures nitrogen dioxide undergoes thermal decomposition into the inert (for purposes of this invention) nitric oxide and molecular oxygen. The decomposition begins at about 150° C. and is complete at about 620° C. The decomposition at various temperatures is as follows:

| Temperature, °C. | 130 | 150 | 184 | 279 | 494 | 620 |
|---|---|---|---|---|---|---|
| Decomposition, % | 0 | 3 | 5 | 13 | 56.5 | 100 |

Thus, at temperatures between about 80° C. and about 300° C., the maximum loss of active nitrogen dioxide by thermal decomposition into inert nitric oxide is only about 15–20%, while at temperatures greater than 300° C., the loss by thermal decomposition rapidly increases to 30% or more, and, finally, to 100% at 620° C. Clearly, the magnitude of the loss of nitrogen dioxide temperatures higher than the usual operating temperatures of this invention and, in particular, the preferred temperature ranges, is wasteful and impractical. Moreover, if recirculation of the effluent stream from such high temperature processes is desired, it is necessary to employ an additional step to reoxidize the inert nitric oxide to the active nitrogen dixide by treatment thereof with oxygen or an oxygen-containing gas such as air, with the attendant added cost and complexity. The additional cost and complexity of this added step, however, is substantially reduced or eliminated altogether by the usual operating temperature conditions employed in the process of this invention.

The vapor phase nitration process of this invention is carried out in the presence of water, which is believed necessary to create and renew reaction sites on the nitration promoting catalyst. The required water can be supplied by water of hydration in the catalyst or, alternatively, by the separate addition of water via the feed stream. When water of hydration is present, no added water is required since once the reaction is initiated, water produced during the course of the reaction (1 mole of water for each 2 moles of nitroaromatic compound produced) is sufficient to sustain it. If the nitration promoting catalyst is substantially anhydrous, it then becomes necessary to add water in an amount sufficient to provide the required reaction sites. Separate addition of water is usually preferred to ensure its presence in sufficient amount. The amount of water present, however, is not narrowly critical. Thus, amounts ranging from nominal or trace amounts up to about 15% by volume of the feed stream are generally sufficient, with amounts ranging from about 0.5% to about 5% by volume being desirably used.

The vapor phase nitration of this invention is conveniently carried out in an apparatus of the type suitable for carrying out chemical reactions in the vapor phase. It can be conducted in a single reactor or in multiple reactors using either a fixed bed, moving bed or a fluidized bed system to effect contacting of the reactants and the nitration promoting catalyst. Reaction is generally carried out by continuously passing a vaporous mixture of the aromatic compound and nitrogen dioxide over a bed of the nitration promoting catalyst phosphorus-vanadium-oxygen complex while maintaining a temperature between about 80° C. and about 300° C., and, usually, about 150° C. to about 225° C.

The reactant aromatic compound can be preheated to form a vapor which is then admixed with gaseous nitrogen dioxide in a suitable reactor in predetermined relative proportions. Vaporous aromatic compounds can be conveniently swept into the reactor at a constant rate by a water-containing stream of carrier gas and thence admixed with a continuous stream of nitrogen dioxide before contacting the heated catalyst bed. The reactants can be charged into the reactor at any suitable flow rate.

As previously indicated, the reactant materials are conveniently swept into the reactor by a stream of carrier gas. The carrier gas employed in the present process can be oxygen or an oxygen-containing gas, for example, air, or an inert gas such as nitrogen, helium, and the like. It is advantageous, however, to employ oxygen or an oxygen-containing gas as the carrier gas due to the stoichiometry of the nitration reaction between the aromatic compound and the nitrogen dioxide.

In the initial nitration reaction between the aromatic compound and the nitrogen dioxide, it is believed that for each 2 moles of aromatic compound, 3 moles of nitrogen dioxide are required to produce 2 moles of nitroaromatic compound, 1 mole of nitric oxide and 1 mole of water. In the absence of an oxygen source such as supplied by the oxygen-containing carrier gas, the nitric oxide is lost, thereby reducing the nitrogen dioxide selectivity to the nitroaromatic compound by at least 33% ($\frac{1}{3}$), as well as the material balance between reactants and recovered products. In the presence of oxygen (and the nitration promoting catalyst), however, the nitric oxide undergoes the known reoxidation to nitrogen dioxide (stoichiometrically requiring 1 mole of oxygen for each 2 moles of nitric oxide), which undergoes further reaction with additional aromatic compound. This known reoxidation of nitric oxide to nitrogen dioxide also serves to reduce the loss of nitrogen dioxide as nitric oxide via the previously discussed nitrogen dioxide thermal decomposition. Overall, therefore, little, if any, nitrogen dioxide is lost by virtue of stoichiometrically produced, as well as thermal produced, nitric oxide.

The concentration of the aromatic compound in the feed mixture is not narrowly critical. All that is necessary is that the concentration be sufficient to permit the reaction to proceed at a reasonable rate. On the other hand, since the nitroaromatic compound produced will have a high vaporization temperature (for example, nitrochlorobenzene isomers, b.p., 235°–246° C.), the concentration should be such that the nitroaromatic compound produced will not condense in the reactor. In addition, since mixtures of aromatic compounds and air (the preferred aromatic compound carrier gas) are potentially flammable and explosive, it is necessary, from a practical viewpoint, to operate at concentrations outside the flammable and explosive limits of the aromatic compound being employed. Generally, concentrations between about 1% and about 15% by volume are desirably employed.

The relative proportions of reactants generally can range from about 1 to 5 moles of nitrogen dioxide per mole of aromatic compound and, preferably, a ratio of about 2 to 3:1 is used. Lower mole ratios can also be employed, if desired, although the conversion may be adversely affected.

The present process is suited to either batch or continuous operation. Continuous operations can involve recirculation of the effluent stream unreacted aromatic compound and nitrogen dioxide following isolation of the nitroaromatic compound product. Additional reactants—aromatic compounds and nitrogen dioxide—can then be charged to the reactor along with the recirculated stream to continue the process in a subsequent and continuous reaction. It will be noted that the substantial absence of side reactions, such as, for example, the thermal decomposition of nitrogen dioxide and undesired by-product formation advantageously facilitate such continuous operations in that extensive purification of the effluent stream is not required and, as previously noted, the cost and complexity of reoxidation of a nitric oxide to nitrogen dioxide is substantially reduced or eliminated altogether.

The nitroaromatic compounds produced during the course of the vapor phase reaction can be collected in a suitable chilled container, and purified by any appropriate method and means known to the art such as, for example, distillation and crystallization. Fractional crystallization in accordance with conventional procedures are especially convenient for the separation of ortho- and para- isomers when a monosubstituted aromatic compound having an ortho-para orientation substituent, such as chlorobenzene, is employed as the reactant or starting material.

The recovered unreacted reactants, due to the substantial absence of side-reactions to produce undesirable by-products, are easily recycled to the reactor for further processing.

The following specific examples illustrating the best presently-known methods of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLES 1–5

Nitration Reactor—A stainless steel tube 40.64 cm (16 inches) in length and 2.54 cm (1 inch) outside diameter, packed with a 35.56 cm (14-inch; approximately 65.5 g) bed of nitration promoting catalyst (prepared as described hereinbelow) was employed as the reactor. The catalyst, unless specified otherwise, was pretreated with nitrogen dioxide at operating conditions (in the absence of the aromatic compounds) to the saturation point, usually from about 5 minutes to about 1 hour.

Catalyst—To a mixture of 340.0 grams (1.87 moles) of vanadium pentoxide, 1150 milliliters of water, and 2.3 grams of Sterox® NJ nonionic surfactant (nonyl-phenol-ethylene oxide condensate, molar ratio of about 1:10) were added 228.0 grams (1.98 moles) of 85% orthophosphoric acid and 173.0 grams (2.06 moles) of 97.6% phosphorous acid. The phosphorus to vanadium atom ratio was about 1.08:1. The aqueous mixture of vanadium and phosphorus compounds was charged to a 2-liter Parr autoclave, fitted with a thermowell, two 6-bladed stirrers, and a vent, and heated to about 100° C. The autoclave was thereafter sealed. The mixture, while being stirred at 1,000 revolutions per minute (rpm), was heated to about 150° C. in about 50±10 minutes and held at this temperature for about 4 hours. After the hold period, the autoclave was cooled to about 80° C. in 50±10 minutes and opened. The aqueous phosphorous-vanadium-oxygen catalyst precursor slurry was placed in an open dish casserole and evaporated to dryness in an oven at 120° C. the remaining solids were ground to pass an 18 mesh sieve (U.S. Standard Sieve Size), mixed with about 20% by weight water, based on the weight of the precursor, to form a viscous putty, which was then extruded through a 0.56-centimeter (0.22-inch) diameter die. The extrudate was cut into pellets of about 0.56 centimeter lengths. The structured putty was allowed to air dry, heated to about 90° C. in an oven to evaporated any remaining water, and then calcined at about 450° C. for about 4 hours to convert the catalyst precursor into the active nitration promotion catalyst.

Nitration Reaction—A stream of aromatic compound was preheated and charged to the reactor tube in a humidified or water-containing stream of air. The nitrating agent, nitrogen dioxide unless otherwise specified, in a nitrogen carrier stream was mixed with the aromatic compound/air stream shortly before contact with the heated catalyst.

The products were collected in a series of three chilled containers, the first of which was chilled in an ice waterbath and the second and third of which were chilled in dry ice baths. Analyses were performed by gas chromatography on a Varian Associated Model 3700 instrument using a 1.83 meter (6 ft.)×0.32 cm (0.125 inch) outside diameter SP-1000 on 0.5% phosphoric acid treated Chrom. G column programmed from 90° C. to 210° C. at a program rate of 10° C./minute.

The parameters and the results are tabulated in Table 1.

TABLE 1

| | CATALYST[1] | | AROMATIC COMPOUND, R—C$_6$H$_5$ | | | | | |
|---|---|---|---|---|---|---|---|---|
| EXAMPLE | Phosphorus/ Vanadium atom ratio | Pretreat. Time min. | R | Flow Rate ml/min | g, moles | Conc. vol. % | Temp. °C. | Carrier Gas[4] Flow Rate ml/min |
| 1 | 1.08/1 | 50 | Cl | 15.80 | 23.8, 0.21 | 2.2 | 75 | 500.0 |
| 2 | " | 10 | " | 16.26 | 14.7, 0.13 | 2.2 | " | " |
| 3 | " | 9 | " | 18.62 | 17.7, 0.17 | 2.6 | " | " |
| 4 | " | — | CH$_3$ | 16.68 | 8.2, 0.089 | 2.4 | 30 | " |
| 5 | " | — | H | 82.50 | 43.1, 0.55 | 10.7 | " | " |

| | NITRATING AGENT[2] | | | | | NITRATING AGENT/AROMATIC COMPOUND |
|---|---|---|---|---|---|---|
| EXAMPLE | Flow Rate ml/min | g, moles | Conc. vol. % | Temp. °C. | Carrier Gas[5] Flow Rate ml/min | molar ratio |
| 1 | 68.73 | 42.3, 0.92 | 9.5 | 15 | 31.0 | 4.38 |
| 2 | 70.48 | 26.1, 0.57 | 9.7 | " | " | 4.38 |
| 3 | 68.49 | 28.1, 0.61 | 9.4 | " | " | 3.57 |
| 4 | 42.41 | 10.4, 0.23 | 6.0 | " | " | 2.58 |
| 5 | 50.90 | 15.7, 0.34 | 6.6 | " | " | 0.62 |

| | WATER | | | | | REACTION CONDITIONS | | |
|---|---|---|---|---|---|---|---|---|
| EXAMPLE | Flow Rate ml/min | g, moles | Conc. vol. % | Temp. °C. | Carrier Gas[4] Flow Rate ml/min | Temp. °C. | Time hours | CONVERSION, %[3] |
| 1 | 10.31 | 2.5, 0.14 | 1.4 | 81 | 99.0 | 200 | 5.0 | 35.6 |
| 2 | 11.13 | 1.6, 0.088 | 1.5 | " | " | 225 | 3.0 | 43.5 |
| 3 | 9.96 | 1.6, 0.088 | 1.4 | " | " | 175 | 3.3 | 38.9 |
| 4 | 21.05 | 2.0, 0.11 | 3.0 | 80 | 98.0 | 175 | 2.0 | 6.8 |
| 5 | 6.97 | 0.8, 0.044 | 0.9 | " | " | 175 | 2.5 | 6.5 |

| | PRODUCTS, % | | | | | | MATERIAL BALANCE | | |
|---|---|---|---|---|---|---|---|---|---|
| | R—C$_6$H$_4$—NO$_2$ | | | | | | g | | |
| | R=H | R=CH$_3$, Cl | | | | | | | |
| EXAMPLE | R=H | ortho | meta | para | Unidentified by- | para/ortho | In | Out | % |
| 1 | — | 10.1 | 0.5 | 25.0 | <0.1 | 2.5 | 68.6 | 68.8 | 100.3 |
| 2 | — | 12.8 | 0.7 | 29.9 | 0.1 | 2.3 | 42.4 | 35.7 | 84.2 |
| 3 | — | 10.6 | 0.4 | 28.0 | <0.1 | 2.6 | 48.4 | 43.4 | 89.7 |
| 4 | — | 3.5 | — | 3.3 | — | 0.9 | 20.6 | 12.6 | 61.2 |

TABLE 1-continued

| | | | | | | | | | |
|---|---|---|---|---|---|---|---|---|---|
| 5 | 6.5 | — | — | — | — | — | 59.6 | 61.2 | 102.7 |

[1] Pretreated for the indicated period of time with nitrogen dioxide at operating conditions (in the absence of the aromatic compound) unless specified otherwise.
[2] Nitrogen dioxide (M.W., 46) unless specified otherwise.
[3] Based on the aromatic compound.
[4] Air
[5] Nitrogen Thus, it is apparent that there has been provided, in accordance with the present invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. In a process for the vapor phase nitration of aromatic compounds selected from the group consisting of monohalobenzenes and aromatic hydrocarbons where the aromatic compound is contacted with a nitrating agent in the vapor phase to yield the corresponding nitroaromatic compound, the improvement comprising conducting the nitration in the presence of a nitration promoting catalyst consisting essentially of a phosphorous-vanadium-oxygen complex wherein the phosphorus-to-vanadium atom ratio in the phosphorus-vanadium-oxygen complex ranges from about 1:2 to about 2:1 and greater than 50 percent of the vanadium is in the tetravalent state.

2. The process improvement of claim 1 wherein the nitrating agent is nitrogen dioxide.

3. The process improvement of claim 1 wherein the nitrating agent is admixed with a carrier gas prior to reaction with the aromatic compound.

4. The process improvement of claim 3 wherein the carrier gas is nitrogen.

5. The process improvement of claim 1 wherein the nitration promoting catalyst is conditioned by pretreatment with the nitrating agent.

6. The process improvement of claim 5 wherein the pretreatment is carried out for about 5 minutes to about 1 hour.

7. The process improvement of claim 1 wherein the aromatic compound is an aromatic hydrocarbon.

8. The process improvement of claim 7 wherein the aromatic hydrocarbon is selected from the group consisting of benzene and toluene.

9. The process improvement of claim 1 wherein the aromatic compound is a monohalobenzene.

10. The process improvement of claim 9 wherein the monohalobenzene is selected from the group consisting of chlorobenzene, bromobenzene, and iodobenzene.

11. The process improvement of claim 1 wherein the concentration of the aromatic compound in the feed mixture is between about 1% and about 15% by volume.

12. The process improvement of claim 1 wherein about 1 to about 5 moles of nitrating agent are used per mole of aromatic compound.

13. The process improvement of claim 1 wherein the aromatic compound is admixed with a carrier gas prior to reaction with the nitrating agent.

14. The process improvement of claim 13 wherein the carrier gas is an oxygen-containing gas.

15. The process improvement of claim 14 wherein the oxygen-containing gas is air.

16. The process improvement of claim 1 wherein water vapor is admixed with the feed mixture prior to reaction between the aromatic compound and the nitrating agent.

17. The process improvement of claim 16 wherein the water vapor is present in the feed mixture in a concentration ranging from nominal amounts up to about 15% by volume.

18. The process improvement of claim 1 wherein the vapor phase reaction is carried out at temperatures ranging from about 80° C. to about 300° C.

19. The process improvement of claim 18 wherein the temperature range is from about 150° C. to about 225° C.

20. The process improvement of claim 10 wherein the monohalobenzene is chlorobenzene and the nitroaromatic compound is a mixture of ortho-, meta-, and para-nitrochlorobenzene.

21. The process improvement of claim 20 wherein the para/ortho isomer ratio is about 2-3/1.

* * * * *